United States Patent [19]
United States Patent [19]

Tindall et al.

[11] Patent Number: 5,045,122
[45] Date of Patent: Sep. 3, 1991

[54] ESTER HYDROLYSIS AND DEPOLYMERIZATION OF POLYESTER AND POLYCARBONATE POLYMERS

[75] Inventors: George W. Tindall, Kingsport; Randall L. Perry, Bluff City, both of Tenn.

[73] Assignee: Eastman Kodak Company, Rochester, N.Y.

[21] Appl. No.: 451,075

[22] Filed: Dec. 14, 1989

[51] Int. Cl.$^5$ ................................................. B08B 3/08
[52] U.S. Cl. ....................................... 134/29; 134/42; 560/79; 562/483; 562/485
[58] Field of Search ................... 560/79, 78; 562/483, 562/485; 134/29, 42

[56] References Cited

U.S. PATENT DOCUMENTS

| | | | |
|---|---|---|---|
| 3,120,561 | 2/1964 | Chambret | 562/483 |
| 3,952,053 | 4/1976 | Brown, Jr. et al. | 562/483 |
| 4,078,143 | 3/1978 | Malik et al. | 560/78 |
| 4,163,860 | 8/1979 | Delattre et al. | 560/96 |
| 4,355,175 | 10/1982 | Puszkaszeri | 562/485 |
| 4,542,239 | 4/1985 | Lamparter et al. | 562/485 |
| 4,578,502 | 3/1986 | Cudmore | 560/79 |
| 4,605,762 | 8/1986 | Mandoki | 562/483 |
| 4,620,032 | 10/1986 | Doerr | 562/483 |
| 4,876,378 | 10/1989 | VanSickle | |

FOREIGN PATENT DOCUMENTS

| | | | |
|---|---|---|---|
| 453369 | 1/1965 | Japan | 585/485 |
| 444338 | 2/1969 | Japan | 585/485 |

OTHER PUBLICATIONS

ASTM Method D 2456 G. G. Esposito, Anal. Chem. 34 (1962) 1173.
D. Vink and R. vanWijk, Z. Anal. Chem. 264 (1973)293.
D. Nissen, V. Rossbach, and H. Zahn, J. Appl. Poly. Sci. 18 (1974)1953 ASTM Method D 2455.
G. G. Esposito and M. H. Swann, Anal. Chem. 34 (1962)1048.
R. Janssen, H. Ruysschaert, and R. Vroom, Makromol Chem. 77(1964)153.
S. J. Jankowski and P. Garner, Anal. Chem. 37 (1965)1709.
J. Rawlinson and E. L. Deeley, J. Oil Col. Chem. Assoc. 50 (1967)373.
P. Perlstein and P. Orme, J. Chromatogr. 351 (1986)203.
J. R. Kirby, A. J. Baldwin, and R. H. Heidener, Anal. Chem. 37 (1965)1306.
J. C. West, Anal. Chem. 47 (1975)1708.
L. H. Ponder, Anal. Chem. 40 (1968)229.
B. J. Allen, G. M. Elsea, K. P. Keller & H. D. Kinder, Anal. Chem. 49 (1977)741.
J. Miller and A. J. Parker, J. Am. Chem. Soc. 83 (1961)117.
J. A. Vinson, J. S. Fritz and C. A. Kingsbury, Talanta, 13 (1966)1673.
N. Isaacs, Physical Organic Chemistry, Longmin Scientific and Technical, Longman Group UK Limited, Essex, England.

*Primary Examiner*—Asok Pal
*Attorney, Agent, or Firm*—Mark A. Montgomery; William P. Heath, Jr.

[57] ABSTRACT

Ester bonds are hydrolyzed, such as in the conversion of polyesters to their monomeric components, by being contacted with a mixture of (a) an alcohol, such as methanol, or glycol, (b) a polar aprotic solvent such as N-methyl-pyrrolidone or dimethyl sulfoxide and (c) an alkoxide or hydroxide such as sodium hydroxide.

26 Claims, No Drawings

ESTER HYDROLYSIS AND DEPOLYMERIZATION OF POLYESTER AND POLYCARBONATE POLYMERS

FIELD OF THE INVENTION

The present invention relates to the hydrolysis of esters and to the recovery of monomeric components from polyester and polycarbonate polymers by a hydrolysis process.

BACKGROUND OF THE INVENTION

The conversion of acids and alcohols to esters is well known, as is the conversion of esters to acids and alcohols. The conversion of many esters to acids and alcohols can be carried out by boiling the ester in a mixture of base and alcohol. However, the conversion of some esters is very difficult as is the conversion of polyesters to their corresponding monomeric acids and glycols. Polyesters are normally not soluble in the solvents that are used for the conversion of esters to alcohol and acid. Also, polyesters are often highly crystallized, further limiting their solubility and hindering the attack of the ester bonds by a base.

Methods are known for the conversion of some polyesters to their monomeric components. These depolymerization methods are generally used to recover monomers from polymer scrap for the repolymerization of the monomers, but can also be used to analyze the polymers to determine their monomer content.

Polyesters can be converted or depolymerized to amides and glycols by a process known as aminolysis. This process entails the refluxing of a polyester with a primary amine or hydrazine such as disclosed in ASTM Method D 2456 and, Anal. Chem. 34 (1962)1173 G. G. Esposito. However, the aminolysis process is generally slow and produces undesirable side reactions with some polyesters.

The transesterification of polyesters is another method of depolymerizing polymers. This method entails heating a polyester in excess alcohol or glycol, optionally in the presence of a catalyst such as disclosed in ASTM Method D 2455 and in Anal. Chem. 37 (1965)1709 J. Jankowski and P. Garner. The transesterification process, however, is generally very slow and high temperatures and pressures are needed to achieve practical conversion rates.

Another method of depolymerizing polyesters is by hydrolysis. This process entails the heating of a polyester with a base in the presence of a solvent, such as an alcohol, such as disclosed in Anal. Chem. 37 (1965)1306, J. R. Kirby, A. J. Baldwin, and R. H. Heidner; U.S. Pat. No. 4,605,762, and U.S. Pat. No. 4,620,032. Hydrolysis, however, is also generally slow at mild conditions, thus, requiring high temperatures and pressures to achieve rapid conversions.

In spite of the many known depolymerization processes, certain polyesters, such as liquid crystalline polyesters, are not easily depolymerizable by any known process.

In light of the above, it would, therefore, be very desirable to rapidly convert substantially all esters to acid and alcohol and to rapidly depolymerize substantially all polyesters and polycarbonates under relatively mild conditions of temperature and pressure without generating undesirable side reactions.

SUMMARY OF THE INVENTION

The process of the present invention rapidly hydrolyzes esters and rapidly depolymerizes polyesters and polycarbonates under relatively mild conditions without generating undesirable side reactions by using a composition comprising a mixture of (a) alcohol or glycol, (b) polar aprotic solvent, and (c) alkoxide or hydroxide. The alkoxide or hydroxide, the alcohol or glycol, and the polar aprotic solvent should be compatible so that the alkoxide or hydroxide will substantially dissolve at relatively high concentrations in the solvent mixture.

DETAILED DESCRIPTION OF THE INVENTION

We have surprisingly found that polyesters and polycarbonates are rapidly converted to their monomeric components by contacting them with a mixture of (a) at least one alcohol, such as methanol, or glycol, (b) at least one polar aprotic solvent such as N-methylpyrrolidone or dimethyl sulfoxide, and (c) at least one alkoxide or hydroxide wherein the alcohol or glycol is capable of dissolving the alkoxide or hydroxide and this solution is in turn soluble in the polar aprotic solvent.

The process of the present invention can be used to cleave any ester bond such as in the recovery of acids or alcohols from esters. The process of the present invention is useful for the hydrolysis of esters that are difficult to hydrolyze and is particularly useful for the depolymerization or conversion to monomeric components of polyesters, and polycarbonates, including copolymers, mixtures thereof and blends of these with other polymers. Highly crystallized polyesters and liquid crystalline polyesters are the most difficult polyesters to depolymerize. However, the process of the present invention depolymerizes these polyesters quite rapidly.

Although we believe that the present invention is useful for the depolymerization of any polyester or polycarbonate, examples of suitable polymers that can be depolymerized by the process of the present invention include: polyethylene terephthalate; bisphenol A polycarbonate; polyethylene 2,6-dinaphthalate; poly-(oxymethylene-1,4-cyclohexylenemethyleneoxycarbonyl-1,4-phenylenediylcarbonyl); and polymers that are prepared from one or more of the following monomers, or esters of these monomers; succinic acid, sebacic acid, azelaic acid, adipic acid, dimer acid, glutaric acid, trans-1,4-cyclohexanedicarboxylic acid, cis,trans-1,4-cyclohexanedicarboxylic acid, 1,3-cyclohexanedicarboxylic acid, isosebacic acid, carbonic acid, pimelic acid, dimethylmalonic acid, suberic acid, 1,12-dodecanedioic acid, terephthalic acid, isophthalic acid, p,p'-methylenedibenzoic acid, 2,6-naphthalenedicarboxylic acid, phthalic acid, dimethyl5-[4-(sodiosulfo)-phenoxy]isophthalate, dimethyl 5-(sodiosulfo)isophthalate, 4,4'-sulfonyldibenzoic acid, 2-(sodiosulfo)-9,9-fluorenebis[propionic acid], 5-[4-(sodiosulfo)phenoxy]isophthalic acid, 5-[(sodiosulfo)propoxy]isophthalic acid, trimellitic acid, 4,4'-stilbene dicarboxylic acid, resorcinol bis acetic acid, 4,4'-biphenyl dicarboxylic acid, ethylene glycol, 1,3-trimethylene glycol, 1,4-butanediol, 1,5-pentanediol, 1,6-hexanediol, 2,2-dimethyl-1,3-propanediol, 1,4-cyclohexanedimethanol, bisphenol A, 2,2,4,4-tetramethyl-1,3-cyclobutanediol, 4,4'-(2-norbornylidene)diphenol, 4,4'-(Hexahydro-4,7-methanoindan-5-ylidene)diphenol, 4,4'-[(3-methyl-2norbornyl)methylene]diphenol, 4,4'-(2-Norbornylidene)- bis(2,6-dichlorophenol), 4,4'-(2-norbornylmethylene)diphenol, 5,6,7,8,-tetrahydro-1,4-naphthalenediol, hydroquinone, t-butyl hydroquinone, diethylene glycol, glycerin, trimethylol propane, trimethylol ethane, poly(tetramethylene glycol), poly(propylene glycol), tischenko glycol, 2,2'-[isopropylidene(p-phenyleneoxy)]diethanol, poly(ethylene glycol)(carbowax) (any molecular weight), poly(oxyethylene oxypropylene) (pluronics) (any molecular weight),4-(hydroxymethyl)cyclohexanecarboxylic acid, hydroxypivalic acid, 6-hydroxyhexanoic acid, and p-hydroxybenzoic acid.

The process of the present invention is useful in the analysis of the monomer content of these polymers; the recovery of monomers from polymer scrap such as bottles, trays, fibers, etc.; the removal of polymer from polymer coated substrates such as dirty polymer processing equipment; and the chemical modification of polymer surfaces by hydrolysis. The process of the present invention is useful for the depolymerization of the polymers in whatever form, such as bulk waste material, since the conversion is rapid and does not require a grinding step. Though the grinding step is not necessary, smaller polymer particles have a larger surface area and are much more rapidly converted to the monomers. Therefore, the particulate form of polymer is more preferred.

The process of the present invention can be conducted at room temperature under mild conditions. However, increased temperature as with increased agitation does reduce conversion time. The upper temperature limit is determined by the capability of the equipment and stability of the products and should not be so high as to decompose the products. The process of the present invention is preferably conducted at a temperature between about room temperature and 200° C. more preferably between about 30° and 200° C. with between about 80° and 150° C. being most preferred. The temperature of the conversion process is dependent upon the reactant materials when the conversion is conducted at refluxing conditions because the temperature is limited by the boiling temperature of the mixture. We have found that as the molecular weight of the alcohol or glycol increases the reflux temperature increases, however, the solubility of the alkoxide or hydroxide in the final solution decreases which tends to reduce the rate of reaction.

The process of the present invention can be conducted at atmospheric pressure. However, elevated pressures increase the boiling or refluxing point of the mixture thereby allowing the temperature to rise and increasing the rate of conversion. The process of the present invention is preferably conducted at a pressure between atmospheric and about 600 psi (about 4,000 kilo pascal, KPa) more preferably between atmospheric and about 220 psi (about 1,500 KPa).

The alcohol or glycol used in the present invention can be any alcohol or glycol that is capable of dissolving the hydroxide or alkoxide. However, the preferred alcohols are $C_1$ to $C_4$ alcohols with methanol being the most preferred and the preferred glycol is ethylene glycol.

Any polar aprotic solvent is useful in the present invention so long as the base (alkoxide or hydroxide) in combination with the alcohol or glycol can be dissolved therein. Examples of suitable polar aprotic solvents include dimethyl formamide, dimethyl sulfoxide, sulfolane, hexamethylphosphoramide, and N-methylpyrrolidone. Dimethyl sulfoxide and N-methylpyrrolidone are most preferred due to their cost, availability, purity, toxicity, and rate of reaction.

The alkoxides or hydroxides useful in the present invention are those that are substantially soluble in the final solution. The preferred alkoxides are $C_1$ to $C_4$ alkoxides. The preferred hydroxides are selected from the group consisting of alkali metal hydroxides, alkaline-earth metal hydroxides, tetra-alkyl ammonium hydroxides, and ammonium hydroxide. In the process of the present invention, the hydroxides are preferred over the alkoxides and the most preferred hydroxides are sodium hydroxide, potassium hydroxide and tetra-alkyl ammonium hydroxide.

For each mole of monomeric diacid unit in the polymer two moles of alkoxide or hydroxide are required for a complete conversion to occur since the acid generally has two ester bonds. However, since the rate of reaction is proportional to the concentration of alkoxide or hydroxide in solution, it is preferred that the alkoxide or hydroxide be in substantial molar excess with respect to the ester bonds in the polymer so that complete conversion of the polymer to the monomers can occur rapidly. The molar ratio of alkoxide or hydroxide to the ester bonds in the polymer is preferably greater than 1/1 with greater than 1.5/1 being more preferred. The upper limit of this molar excess is limited by the solubility of the alkoxide or hydroxide in the mixture. However, an amount in excess of this can be present as solid in the mixture to enter solution as alkoxide or hydroxide is depleted.

We have found that the alcohol or glycol functions to enhance the solubility of the alkoxide or hydroxide in the polar aprotic solvent. Its concentration in the mixture should be high enough to dissolve sufficient hydroxide or alkoxide so that the reaction proceeds at a rapid rate. However, excess alcohol or glycol is detrimental because it dilutes the beneficial effect of the polar aprotic solvent.

We have found that the presence of the polar aprotic solvent enhances the rate of reaction above that which can be achieved by the mixture of alcohol or glycol and alkoxide or hydroxide alone. Hence, a high concentration of polar aprotic solvent is desirable. However, hydroxides and alkoxides are generally not as soluble in polar aprotic solvents as they are in alcohols and glycols. If the concentration of polar aprotic solvent becomes too large the concentration of hydroxide or alkoxide in solution will decrease to the point where the beneficial effects of increasing the concentration of the polar aprotic solvent will be cancelled by a decrease in hydroxide or alkoxide concentration. These effects are illustrated for methanol and dimethyl sulfoxide in Example 9.

In light of what we have discovered the preferred ratio of polar aprotic solvent to alcohol or glycol will vary depending upon which polar aprotic solvent, alcohol or glycol, or hydroxide or alkoxide is used. In each case, the fastest reaction rates will be determined by a compromise between increasing the hydroxide or alkoxide solubility by the alcohol or glycol and enhancing the rate by maximizing the concentration of the polar aprotic solvent.

For example, when the components are as follows: dimethyl sulfoxide or N-methylpyrrolidone as the polar aprotic solvent; sodium or potassium hydroxide as the alkoxide or hydroxide; and methanol as the alcohol or glycol, the preferred amounts of components are as follows: between about 10 and 99 volume % polar aprotic solvent; between about 0.5 molar and a saturated solution of hydroxide; and between about 90 and 1 volume % methanol. The more preferred amounts of these are 20 and 95 volume % dimethylsulfoxide or N-methylpyrrolidone and 80 and 5 volume % methanol, saturated with hydroxide.

In some instances complete conversion of all polymer may not be desirable, such as in smoothing a rough polymer surface and in chemically modifying a polymer surface by hydrolysis such as in fiber or film treatment. If this is desired, the polymer is simply removed from contact with the solution when sufficient depolymerization has occurred.

The sequential addition of the components of the mixture or solution used in the process of the present invention is not critical. However, it is preferred that the alkoxide or hydroxide be dissolved in the alcohol or glycol prior to the addition of the polar aprotic solvent which is then followed by the addition of the polymer.

The container or reactor used in conducting the process of the present invention is not critical; however, it is preferred that the process of the present invention be conducted in a container in the presence of agitation such as a stirred batch reactor or a continuous reactor. Though not critical the use of a continuous reactor is the more preferred method of employing the process of the present invention. Conducting the process of the present invention in a continuous process is a major advantage over high pressure reactors which must be conducted batch wise.

At the completion of the reaction (conversion) the acid monomers are usually in the form of salts of the acids and are usually insoluble in the reaction mixture. These insoluble salts can be recovered by any conventional process such as by filtration. The recovered monomer salts can be converted back to their acid form by the addition of acid. Alternatively, if it is desired the acid monomer can be separated from the solution by the addition of acid to precipitate the acids followed by filtration recovery.

The process of the present invention is preferably conducted in the absence of water. Anhydrous conditions are preferred since the rate of conversion decreases as the amount of water increases.

The major advantage of the process of the present invention over conventional processes is the increased rate of conversion at relatively mild conditions of pressure and temperature.

The following examples are presented to illustrate the present invention but are not intended to limit the reasonable scope thereof.

EXAMPLES

EXAMPLE 1

One mL of a 5 molar sodium hydroxide in methanol solution was added to four mL of dimethyl sulfoxide (DMSO). A 0.25 g sample of polyethylene terephthalate pellets (identified as Kodapak PET from Eastman Chemical Company), approximately 3 mm × 3 mm × 3 mm, was added to this solution and the resulting mixture was stirred and heated at reflux. Within about 6 minutes the pellets had disappeared and a white solid separated from the solution. This solid was identified as the disodium salt of terephthalic acid.

EXAMPLE 2

One mL of a 5 molar sodium hydroxide in deuterated methanol solution was added to four mL of deuterated dimethyl sulfoxide. A 0.25 g sample of the polyethylene terephthalate pellets of Example 1, was added to this solution and the resulting mixture was stirred and heated at reflux. Within about 6 minutes the pellets had disappeared and the white solid disodium salt of terephthalic acid separated from the solution. Three mL of deuterium oxide were added to dissolve the sodium terephthalate. Deuterated solvents were used to enable analysis of the mixture by proton nuclear magnetic resonance. Analysis of the solution by proton nuclear magnetic resonance revealed that all detectable ester bonds had cleaved. The only detectable products were ethylene glycol and sodium terephthalate which indicated complete conversion of the polyester to its monomeric components.

EXAMPLE 3

The process according to Example 2 was repeated with potassium hydroxide instead of sodium hydroxide. Analysis by proton magnetic resonance revealed all ester bonds had cleaved within about 6 minutes. The only detectable products were ethylene glycol and potassium terephthalate.

EXAMPLE 4

2.5 mL of a 2.75 molar solution of tetramethyl ammonium hydroxide in methanol was added to 2.5 mL of dimethyl sulfoxide. A 0.25 g sample of the polyethylene terephthalate pellets, of Example 1, was added to this solution and the resulting mixture was stirred and heated at reflux. Within about 5 minutes the pellets were converted to the monomeric components. In this case the salts of the terephthalic acid were soluble.

EXAMPLE 5

One mL of a 5 molar sodium hydroxide in methanol solution was added to four mL of N-methylpyrrolidone. A 0.25 g sample of the polyethylene terephthalate pellets of Example 1, was added to this solution and the resulting mixture was stirred and heated at reflux. Within about 7 minutes the pellets had disappeared and sodium terephthalate and ethylene glycol were formed. These products were identified by chromatographic analysis retention times.

EXAMPLE 6

One mL of a 5 molar sodium hydroxide in methanol solution was added to four mL of dimethyl sulfoxide. A 0.25 g sample of bisphenol A polycarbonate pellets (identified as Mobay Makrolon 2600 from Mobay Chemical Company), approximately 3 mm × 3 mm × 3 mm was added to this solution and the resulting mixture was stirred and heated at reflux. Within about three minutes the sample was converted to its monomeric components.

EXAMPLE 7

One mL of a 5 molar sodium hydroxide in methanol solution was added to four mL of dimethyl sulfoxide. A 0.25 g sample of highly crystallized polyethylene 1,6-dinaphthalate pellets, approximately 3 mm × 3 mm × 3mm was added to this solution and the resulting mixture was stirred and heated at reflux. Within about 26 minutes the pellets had disappeared completely, and were converted to the monomeric components (corresponding acid salt and glycol).

EXAMPLE 8

The process according to Example 1 was repeated using 1 molar potassium hydroxide and an alcohol or glycol other than methanol. The results are listed in the following table:

TABLE 1

| Solvent in Vol. % | Conversion Time in Minutes |
|---|---|
| DMSO/Ethanol 50/50 | 13 |
| DMSO/n-propanol 50/50 | 15 |
| DMSO/Ethylene glycol 80/20 | 25 |
| DMSO/Ethylene Glycol 50/50 | 125 |

EXAMPLE 9

The process according to Example 1 was repeated using 1 molar sodium hydroxide and various volume percents of dimethyl sulfoxide and methanol. The results are listed in the following table:

TABLE 2

| | Vol % Methanol | | | | | | | | |
|---|---|---|---|---|---|---|---|---|---|
| | 0 | 10 | 20 | 40 | 60 | 70 | 80 | 90 | 100 |
| Conversion Time in Min. | 128 (a) | 11 (a) | 7 | 10 | 42 | 76 | 150 | 356 | (b) |

(a) Initially the sodium hydroxide was not completely dissolved in this solution
(b) After 8 hours this conversion was not complete

EXAMPLE 10 COMPARATIVE

This example illustrates one of the fastest conventional approaches to convert polyethylene terephthalate to ethylene glycol and terephthalic acid. A 0.25 g sample of the polyethylene terephthalate of Example 1 was stirred and refluxed in 5 mL of a 1 molar solution of potassium hydroxide in n-propanol. It took 60 minutes to convert the polymer to its monomeric components as compared to 6 minutes in Example 3.

EXAMPLE 11 COMPARATIVE

This example also illustrates the conventional approach of Example 10 on a different polymer. A 0.25 g sample of crystallized polyethylene 2,6-dinaphthalate pellets was stirred and refluxed in 5 mL of a 1 molar solution of potassium hydroxide in n-propanol. After 6 hours the polymer was barely affected as compared to 26 minutes for complete conversion in Example 7.

EXAMPLE 12 COMPARATIVE

A 0.2 g sample of the polyethylene terephthalate of Example 1 was placed in a Paar pressure bomb with 10 mL of methanol and 1 μl of titanium isopropoxide catalyst. The bomb was heated at 200° C. It took three hours to convert the polymer to its monomeric components as compared to 6 minutes in Example 1.

EXAMPLE 13

The purpose of this example was to measure the effect of water on the reaction. Three 0.25 g samples of the polyethylene terephthalate of Example 1 were added to separate solutions made from one mL of a 5 molar sodium hydroxide in methanol solution and four mL of dimethyl sulfoxide. This mixture was stirred and heated at reflux until the polymer reacted to form its monomeric components as determined by the disappearance of the polymer pellets. This time was recorded. The experiment was repeated using three 0.25 g samples with increasing amounts of water. The average times for complete reaction of the three samples are given in Table 3.

TABLE 3

Effect of Water on the Conversion Time of Polyethylene Terephthalate to its Monomeric Components
Average Hydrolysis Time

| 0% Water | 1% Water | 2% Water | 5% Water |
|---|---|---|---|
| 5 Min. | 6 Min. | 7 Min. | 17 Min. |

EXAMPLE 14

The process of Example 2 was repeated substituting the sample of polyethylene terephthalate pellets with the same amount of a liquid crystalline polyester prepared from terephthalic acid, ethylene glycol, and para hydroxybenzoic acid in a molar ratio of 20:20:80. This sample was converted to its monomeric components in about 7 minutes.

EXAMPLE 15

The process of Example 1 was repeated substituting the sample of polyethylene terephthalate pellets with the same amount of polyester pellets prepared from the monomers listed in Table 4.

TABLE 4

| Monomers(a) | | Conversion Time in the Polar Aprotic Solvent | |
|---|---|---|---|
| Acid | Glycol | DMSO | N-Methylpyrrolidone |
| Terephthalic acid 100 mol % | 1,4-cyclohexanedimethanol 100 mol % | 14 min | 15 min |
| Terephthalic acid 70 mol % and 1,4-cyclohexane dicarboxylic acid 30 mol % | 1,4-cyclohexanedimethanol 100 mol % | 13 min | 10 min |

(a) In the polymerization... total as 100 mol %... and the glycol as...

The ester bonds between the 1,4-cyclohexanedicarboxylic acid and the 1,4-cyclohexanedimethanol are sterically hindered and hence are very difficult to hydrolyze using sodium hydroxide in n-propanol, according to the conventional process. This example further illustrates the usefulness of the process of the present invention for the hydrolysis of difficult to hydrolyze esters and polyesters since this polymer is readily hydrolyzed by this process.

EXAMPLE 16

This example illustrates the use of the present invention in hydrolyzing monomeric esters that are normally difficult to hydrolyze. Four mL of dimethyl sulfoxide and 1 mL of a 5 molar sodium hydroxide in methanol solution were added to a 0.1 g sample of a fungus identified as geotrichum candidum (ATCC-6005). This solution was heated and stirred at 100° C. for 10 minutes. Analysis of the solution revealed that twice the amount of ergosterol steroid was hydrolyzed from the cells than was hydrolyzed under these conditions by the traditional method which uses alcoholic KOH.

As it can be seen the process of the present invention surprisingly decreases the hydrolysis time of ester bonds, including those in polyesters and polycarbonates, at relatively mild conditions.

The present invention has been described in detail with particular references to preferred embodiments thereof. However, variations and modifications can be affected within the scope of the present invention without departing from the spirit thereof.

We claim:

1. A process for the hydrolysis of esters comprising contacting at least one ester with a mixture of (a) at least one alcohol or glycol; (b) at least one polar aprotic solvent; and (c) at least one alkoxide or hydroxide for a sufficient time to convert said ester to its corresponding alcohol or glycol and its corresponding acid or acid salt, wherein said alcohol or glycol is capable of bringing at least a portion of said alkoxide or hydroxide into solution with said polar aprotic solvent.

2. The process according to claim 1 wherein said ester is selected from esters that are difficult to hydrolyze in only alcohol and base.

3. A process for the conversion of polymers to their monomeric components comprising contacting a polymer selected from the group consisting of polyesters, polycarbonates, and mixtures thereof with a mixture of (a) at least one alcohol or glycol; (b) at least one polar aprotic solvent; and (c) at least one alkoxide or hydroxide for a sufficient time to convert at least a portion of said polymer to it's monomeric components; wherein said alcohol or glycol is capable of bringing at least a portion of said alkoxide or hydroxide into solution with said polar aprotic solvent.

4. The process according to claim 3 wherein the amount of component (a) is between about 5 and 80 volume and the amount of component (b) is between about 95 and 20 volume %.

5. The process according to claim 4 wherein component (c) is in a concentration between 0.5 molar and saturated condition in the solvent mixture of components (a) and (b).

6. The process according to claim 3 wherein said polymer is selected from liquid crystalline polyesters.

7. The process according to claim 3 wherein said polymer is in the form of waste material.

8. The process according to claim 3 wherein said polymer is in particulate form.

9. The process according to claim 3 wherein said polymer is adhered to a substrate.

10. The process according to claim 9 wherein said substrate is a piece of polymer processing equipment.

11. The process according to claim 3 wherein only the surface of said polymer is hydrolyzed.

12. The process according to claim 11 wherein said polymer is in the form of fiber or film.

13. The process according to claim 3 wherein said alcohol is selected from the group consisting of C1 to C4 alcohols; said glycol is ethylene glycol; said polar aprotic solvent is selected from dimethyl formamide, dimethyl sulfoxide, sulfolane, hexamethylphosphoramide, and N-methylpyrrolidone; said alkoxide is elected from the group consisting of $C_1$ to $C_4$ alkoxides; and said hydroxide is selected from the group consisting of alkali metal hydroxides, alkaline-earth metal hydroxides, tetra-alkyl ammonium hydroxide, and ammonium hydroxide.

14. The process according to claim 3 wherein said alcohol or glycol is selected from the group consisting of $C_1$ to $C_4$ alcohols.

15. The process according to claim 14 wherein said alcohol or glycol is methanol; said polar aprotic solvent is selected from dimethyl sulfoxide and N-methylpyrrolidone; and said alkoxide or hydroxide is selected from the group consisting of sodium hydroxide, potassium hydroxide or tetra alkyl ammonium hydroxide.

16. The process according to claim 3 wherein said polymer is contacted with said mixture at a temperature between about room temperature and about 200° C. and a pressure between atmospheric and about 600 psi (about 4,000 KPa).

17. The process according to claim 16 wherein said polymer is contacted with said mixture at a temperature between about 80° and 150° C.

18. The process according to claim 17 wherein said polymer is contacted with said mixture at a pressure between atmospheric and about 220 psi (about 1,500 KPa).

19. The process according to claim 3 wherein said mixture is in substantially anhydrous conditions.

20. The process according to claim 3 wherein said alkoxide or hydroxide is dissolved in said alcohol or glycol prior to the addition of said polar aprotic solvent.

21. The process according to claim 3 wherein said polymer is removed from contact with said mixture after a portion of the surface of said polymer has been converted to its monomeric components.

22. The process according to claim 3 wherein said alkoxide or hydroxide is present in a molar excess with respect to ester bonds in said polymer.

23. A process for the conversion of polymers to their monomeric components comprising contacting a composition containing a polymer selected from the group consisting of polyesters and polycarbonates with a mixture of (a) about 5 to 80 (vol) % methanol, (b) about 95 to 20 (vol) % of a polar aprotic solvent selected from the group consisting of dimethyl sulfoxide and N-methylpyrrolidone, and (c) an alkali metal hydroxide in molar excess, with respect to the ester bonds to be hydrolyzed, at a temperature between about room temperature and reflux conditions for a sufficient time to convert at least a portion of said polymer to its monomeric components.

24. The process according to claim 23 wherein said mixture is in substantially anhydrous conditions.

25. The process according to claim 23 wherein said polymer is selected from liquid crystalline polyesters.

26. A process for removing a polymer from a substrate comprising contacting a polymer coated substrate with a mixture of (a) at least one alcohol or glycol; (b) at least one polar aprotic solvent; and (c) at least one alkoxide or hydroxide; wherein said polymer is selected from the group consisting of polyesters, polycarbonates, and mixtures thereof and said alcohol or glycol is capable of bringing at least a portion of said alkoxide or hydroxide into solution with said polar aprotic solvent.

* * * * *